US011994374B2

(12) United States Patent
Dotan et al.

(10) Patent No.: US 11,994,374 B2
(45) Date of Patent: May 28, 2024

(54) INTEGRATED MEASUREMENT SYSTEM

(71) Applicant: NOVA LTD., Rehovot (IL)

(72) Inventors: Elad Dotan, Talmei Yehiel (IL); Moshe Vanhotsker, Rehovot (IL); Shimon Yalov, Rehovot (IL); Valery Deich, Rehovot (IL); Roi Ringel, Rehovot (IL); Beni Shulman, Rehovot (IL); Yosi Bar On, Rehovot (IL); Shahar Bassan, Rehovot (IL)

(73) Assignee: NOVA LTD., Rehovot (IL)

( * ) Notice: Subject to any disclaimer, the term of this patent is extended or adjusted under 35 U.S.C. 154(b) by 403 days.

(21) Appl. No.: 17/309,318

(22) PCT Filed: Nov. 17, 2019

(86) PCT No.: PCT/IL2019/051253
§ 371 (c)(1),
(2) Date: May 18, 2021

(87) PCT Pub. No.: WO2020/105036
PCT Pub. Date: May 28, 2020

(65) Prior Publication Data
US 2021/0396511 A1    Dec. 23, 2021

(30) Foreign Application Priority Data
Nov. 19, 2018 (IL) .......................... 263106

(51) Int. Cl.
G01B 11/02    (2006.01)
G01B 5/00    (2006.01)
(Continued)

(52) U.S. Cl.
CPC ............ G01B 11/02 (2013.01); G01B 5/0004 (2013.01); G01N 21/8806 (2013.01);
(Continued)

(58) Field of Classification Search
CPC ..... G01B 11/02; G01B 11/022; G01B 11/024; G01B 11/026; G01B 11/028; G01B 11/06;
(Continued)

(56) References Cited

U.S. PATENT DOCUMENTS 5,377,000 A * 12/1994 Berends ................... G01J 3/51
356/73
5,648,849 A * 7/1997 Canteloup ............ B24B 37/013
356/451

(Continued)

FOREIGN PATENT DOCUMENTS

CN    1793860 A    6/2006
CN    107850555 B    6/2023
(Continued)

Primary Examiner — Gordon J Stock, Jr.
(74) Attorney, Agent, or Firm — Reches Patents

(57) ABSTRACT

A measurement system is presented configured for integration with a processing equipment for applying optical measurements to a structure. The measurement system comprises: a support assembly for holding a structure under measurements in a measurement plane, configured and operable for rotation in a plane parallel to the measurement plane and for movement along a first lateral axis in said measurement plane; an optical system defining illumination and collection light channels of normal and oblique optical schemes and comprising an optical head comprising at least three lens units located in the illumination and collection channels; a holder assembly comprising: a support unit for carrying the optical head, and a guiding unit for guiding a sliding movement of the support unit along a path extending along a second lateral axis perpendicular to said first lateral axis; and an optical window arrangement comprising at least three optical windows made in a faceplate located between the optical head at a certain distance from the measurement plane. The optical windows are aligned with the illumination (Continued)

and collection channels for, respectively, propagation of illuminating light from the optical head and propagation of light returned from an illuminated region to the optical head, in accordance with the normal and oblique optical schemes.

21 Claims, 7 Drawing Sheets

(51) Int. Cl.
| | |
|---|---|
| *G01N 21/84* | (2006.01) |
| *G01N 21/88* | (2006.01) |
| *G01N 21/95* | (2006.01) |
| *G01N 21/956* | (2006.01) |
| *G03F 7/00* | (2006.01) |
| *H01L 21/66* | (2006.01) |

(52) U.S. Cl.
CPC ....... *G01N 21/9501* (2013.01); *G01N 21/956* (2013.01); *G03F 7/70625* (2013.01); *G03F 7/706849* (2023.05); *G03F 7/706851* (2023.05); *H01L 22/12* (2013.01); *G01N 2021/8411* (2013.01); *G01N 2021/8825* (2013.01)

(58) Field of Classification Search
CPC ............ G01B 11/0616; G01B 11/0625; G01B 11/0633; G01B 11/0641; G01B 11/065; G01B 11/0683; G01B 11/08; G01B 11/11; G01B 11/16; G01B 11/22; G01B 11/24; G01B 11/26; G01B 11/27; G01B 11/272; G01B 11/28; G01B 11/285; G01B 11/30; G01B 11/303; G01B 11/306; G01B 5/0002; G01B 5/0004; H01L 22/00; H01L 22/10; H01L 22/12; H01L 22/2024; H01L 22/26; H01L 22/30; G01N 21/84; G01N 21/8422; G01N 21/86; G01N 21/88; G01N 21/8803; G01N 21/8806; G01N 21/8851; G01N 21/89; G01N 21/8901; G01N 21/8903; G01N 21/8914; G01N 21/892; G01N 21/95; G01N 21/9501; G01N 21/9503; G01N 21/9505; G01N 21/9506; G01N 21/956; G01N 21/95607; G01N 2021/8411; G01N 2021/8416; G01N 2021/8427; G01N 2021/845; G01N 2021/8461; G01N 2021/8609; G01N 2021/8645; G01N 2021/8654; G01N 2021/8822; G01N 2021/8825; G01N 2021/8845; G01N 2021/8848; G01N 2021/8854; G01N 2021/8867; G01N 2021/887; G01N 2021/9511; G01N 2021/9513; G03F 7/70605; G03F 7/70608; G03F 7/70616; G03F 7/70625; G03F 7/70633; G03F 7/70641; G03F 7/7065; G03F 7/70653; G03F 7/70681; G03F 7/706843; G03F 7/706849; G03F 7/706851

See application file for complete search history.

(56) References Cited

U.S. PATENT DOCUMENTS

| | | | |
|---|---|---|---|
| 6,247,998 B1* | 6/2001 | Wiswesser | B24B 37/013 451/6 |
| 6,392,745 B1* | 5/2002 | Mavliev | G01N 21/9501 356/37 |
| 6,426,502 B1* | 7/2002 | Finarov | H01L 21/681 250/559.23 |
| 6,695,947 B2* | 2/2004 | Eriguchi | H01L 21/67167 156/345.31 |
| 7,195,535 B1* | 3/2007 | Swedek | B24B 49/12 451/6 |
| 7,420,681 B1* | 9/2008 | Wang | G01N 21/211 356/369 |
| 8,248,606 B1* | 8/2012 | Liphardt | G01N 21/211 356/369 |
| 8,513,625 B2* | 8/2013 | Dana | G03F 7/70633 250/306 |
| 9,553,034 B1* | 1/2017 | Young | H01L 22/12 |
| 9,772,183 B2* | 9/2017 | Stefanczyk | G01B 11/005 |
| 10,451,542 B2* | 10/2019 | Doyle | G03F 1/84 |
| 10,739,277 B2* | 8/2020 | Berlatzky | G01N 21/8806 |
| 10,884,227 B2* | 1/2021 | Tomer | G02B 21/0032 |
| 10,969,329 B2* | 4/2021 | Lim | G01N 21/211 |
| 10,978,278 B2* | 4/2021 | Meng | H01L 21/67253 |
| 11,398,393 B2* | 7/2022 | Lin | H01L 21/268 |
| 2015/0128860 A1* | 5/2015 | Canizares | C23C 16/52 118/712 |
| 2018/0149603 A1 | 5/2018 | Bhattacharyya et al. | |
| 2018/0217065 A1 | 8/2018 | Haller | |

FOREIGN PATENT DOCUMENTS

| | | |
|---|---|---|
| JP | 2000117482 | 4/2000 |
| JP | 2000117482 A | 4/2000 |
| TW | 200702656 A | 1/2007 |
| TW | 201643405 B | 10/2019 |

* cited by examiner (GENERAL ART)

(GENERAL ART)

(GENERAL ART)

INTEGRATED MEASUREMENT SYSTEM

TECHNOLOGICAL FIELD AND BACKGROUND

The present invention is in the field of measurement techniques, and relates to an optical measurement system for use in integrated measurement/monitoring systems, which is particularly useful in semiconductor industry.

The manufacture of semiconductor devices consists of a multi-staged process requiring wafers progressing on a production line to be measured between sequential manufacturing steps. The current trends of shrinking dimensions in the semiconductors industry and the dynamic nature of the processes involved in the semiconductor manufacturing, increase the need for accurate diagnostic tools, capable of providing close to real time measurements for short time to-respond feedback loops, such as closed loop control and feed forward control. Such stringent requirements cannot be obtained by off-line ("stand alone") measuring systems, which do not provide a real time response, and cannot be provided by in-situ detection devices, such as end-point detection devices, as their performance is not accurate enough.

Integrated measurement/monitoring techniques have been developed, providing physical implementation of monitoring tools, with full metrology capabilities, within the production line in the semiconductor fabrication plant. Integrated measurement system is a system that is physically installed inside the processing equipment or is attached to it and is dedicated to a specific process.

Integrated measurement systems are to be considered from several aspects and meet specific requirements in order to be feasible. Such requirements include inter alia the following: a small footprint, i.e. integrated measurement system should have as small footprint as possible in order to be physically within the processing equipment (e.g., installed inside the processing equipment or connected to Equipment Front End Module (EFEM) via load ports) such as CMP equipment for example, separation of a measuring unit from the environment of the processing equipment (e.g., using sealed enclosure); high speed measuring unit (e.g., fast positioning, autofocusing and measurement); having the option to be bypassed by the production process and to operate at off-line mode; etc.

Various integrated measurement/metrology systems have been developed and are widely used, being commercially available from the assignee of the present application, such as NovaScan® 3090Next, NOVA i500®, etc.

GENERAL DESCRIPTION

There is a need in the art for a novel integrated measurement system for optical measurements on patterned structures, especially complex structures, enabling optical critical dimension (OCD) measurements using both normal and oblique measurement schemes.

In many cases it is advantageous to perform optical wafer metrology measurements with both normal and oblique schemes, to increase the number of the measurement channels. Indeed, measurements with normal and oblique measurement schemes could provide more complete information about the structure being measured.

Considering metrology system, in particular for OCD measurements on complex patterned structure, provision of such additional information from different measurement schemes is important. This is because measurements with the normal and oblique measurement schemes may be of different sensitivities to different structure parameters, and thus when used in combination increase the amount of information about the structure under measurements. Further, combining the normal and oblique measurement schemes facilitates addition of further measurement channels, for example the use of different orientations of the plane of polarization of light relative to the patterns in the normal incidence scheme, and/or the use of different azimuths of light incidence.

The present invention provides a novel optical integrated metrology system, mainly for OCD measurements, whose design/configuration is optimized such that it, on the one hand, is sufficiently compact (has small footprint) to be used with a processing equipment, and, on the other hand, is configured with both the normal and oblique measurement schemes, being effectively switched between these two operational schemes, thus enabling measurements with different measurement conditions. As described above, these different measurement conditions may include for example azimuth variation in the oblique incidence scheme and/or polarization variation in the normal incidence scheme.

The integrated metrology system of the invention may advantageously be used for measurements on symmetrical structures, namely structures having a geometrical contour having an axis of symmetry, such as disk-like structures, which can be measured half-by-half by implementing 180-degree rotation of the structure-carrying stage with respect to the measuring optics.

Thus, according to one broad aspect of the invention, it provides a measurement system which comprises:

a support assembly for holding a structure under measurements in a measurement plane, the support assembly being configured and operable for rotation in a plane parallel to the measurement plane and for movement along a first lateral axis in said measurement plane;

an optical system defining illumination and collection light channels of normal and oblique optical schemes; the optical system comprising an optical head comprising at least three lens units located in the illumination and collection channels;

a holder assembly comprising: a support unit for carrying the optical head, and a guiding unit configured and operable for guiding a sliding movement of the support unit along a path extending along a second lateral axis perpendicular to said first lateral axis; and an optical window arrangement comprising at least three optical windows made in a faceplate located between the optical head at a certain distance from the measurement plane, the windows being arranged in spaced-apart parallel relationship and extending parallel to said path, said optical windows being aligned with the illumination and collection channels for, respectively, propagation of illuminating light from the optical head and propagation of light returned from an illuminated region to the optical head, in accordance with said normal and oblique optical schemes.

The measurement system may further include a controller configured and operable to controllably shift the optical system operation between the normal and oblique optical schemes.

In some embodiments, the measurement system includes a navigation movement system configured and operable to drive rotational movement of the support assembly and the movements of the support assembly and the support unit of the holder assembly along said first and second lateral axes, respectively.

In some embodiments, the optical system includes a common light source optically coupled with the illumination channels of the normal and oblique optical schemes, and separate detection devices accommodated in the respective collection channels of the normal and oblique optical schemes.

In some embodiments, each of the collection channels is configured for directing the collected specularly returned light to spatially separated imaging and measurement channels. For example, each of the collection channels may include a pinhole mirror device for spatially separating the collected light into imaging and measurement light portions and directing them to propagate through the imaging and measurement channels.

The imaging and measurement channels may be optically coupled to imaging and measurement detection devices. Alternatively, the measurement channels may include optical fibers. In either of these configurations or both of them, the measurement channels of the normal and oblique optical schemes may be optically coupled to the same spectrometric detector.

In some embodiments, the optical head of the optical system includes at least three objective lens units located in, respectively, the normal and oblique optical schemes. The objective lens units are preferably configured with low chromatic aberrations.

In some embodiments, the optical system comprises a polarizing assembly including at least one polarizer located in at least one of the illumination and collection channels.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

As described above, the present invention provides a measurement system configured for integration with a processing equipment for applying optical measurements to structures before or after being processed by the processing equipment. The processing equipment may include one or more processing tools, and a structure progresses through successive stages of the processing equipment, while the measurement system may apply measurements to the structure before or after at least some of the processing stages. As described above, in some cases, an integrated measurement system could be located inside the processing equipment, and in some other cases an integrated measurement system is connected to an Equipment Front End Module (EFEM) via a load port. In the description below, the integrated measurement/metrology system is described as being integrated with or within a processing equipment, to cover any of such possible configurations.

Figure 1:
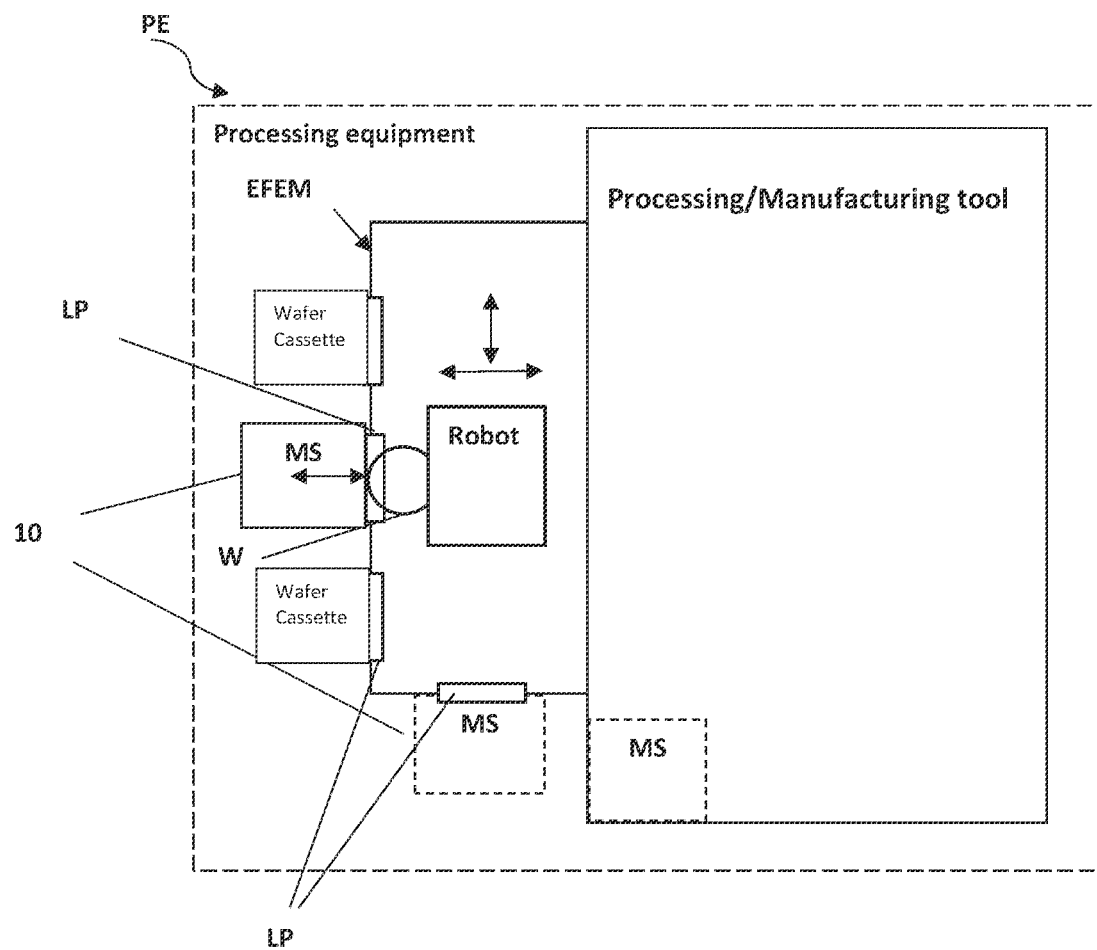
FIG. 1 is a schematic illustration of an example of integration of a measurement/metrology system with a processing equipment.

In this connection, reference is made to FIG. 1, exemplifying, by way of a. block diagram, integration of a measurement system (MS) 10 with a processing equipment PE (e.g. material removal (CMP, Etch) or deposition (CVD) equipment). In this example, the processing equipment PE includes a processing/manufacturing tool. and its associated EFE.M. The EFEM typically has a number of load ports LP associated with a corresponding number of wafer cassette unit(s), and a robot R (or number of robots) for transporting the structuresRvafers W from the load port of the cassette unit to the processing tool. The integrated measurement system(s) 10 is/are accommodated within the processing equipment, e,g. within the processing tool. station, and/or at the EFEM side (similar to the cassette station, having a load port), and the same robots) truly be used for transporting the wafer via the respective load port 1,P onto a holder or support stage of the measurement system 10. Typically, the holder (or gripper/chuck) is part of a structure handling assembly.

The construction and operation of the processing equipment, as well as those of structure transport and holding means, do not form part of the present invention, and therefore need not be specifically described, except to note the following. In order to control the processes being applied to the structure in the processing equipment PE, measurements are applied to the structure after being processed by the processing tool and/or prior to be processed by the processing tool, and by this control the process(es) being applied to the structure, i.e. control the working parameters of the processing tool(s). The measured data provided by the integrated measurement system may thus be utilized in a closed-loop process control providing feed-back results for a specific processing tool in case the measurements are applied after processing, and/or providing feed-forward results for a specific processing tool in case the measurements are applied to the structure prior to be processed by said tool, e.g. to define initial conditions in the beginning of the process. For example, the processing equipment PE may be that of Chemical Mechanical Planarization (CMP), and the integrated metrology system 10 may perform post-CMP measurements and possibly also pre-CMP measurements.

Figure 2:
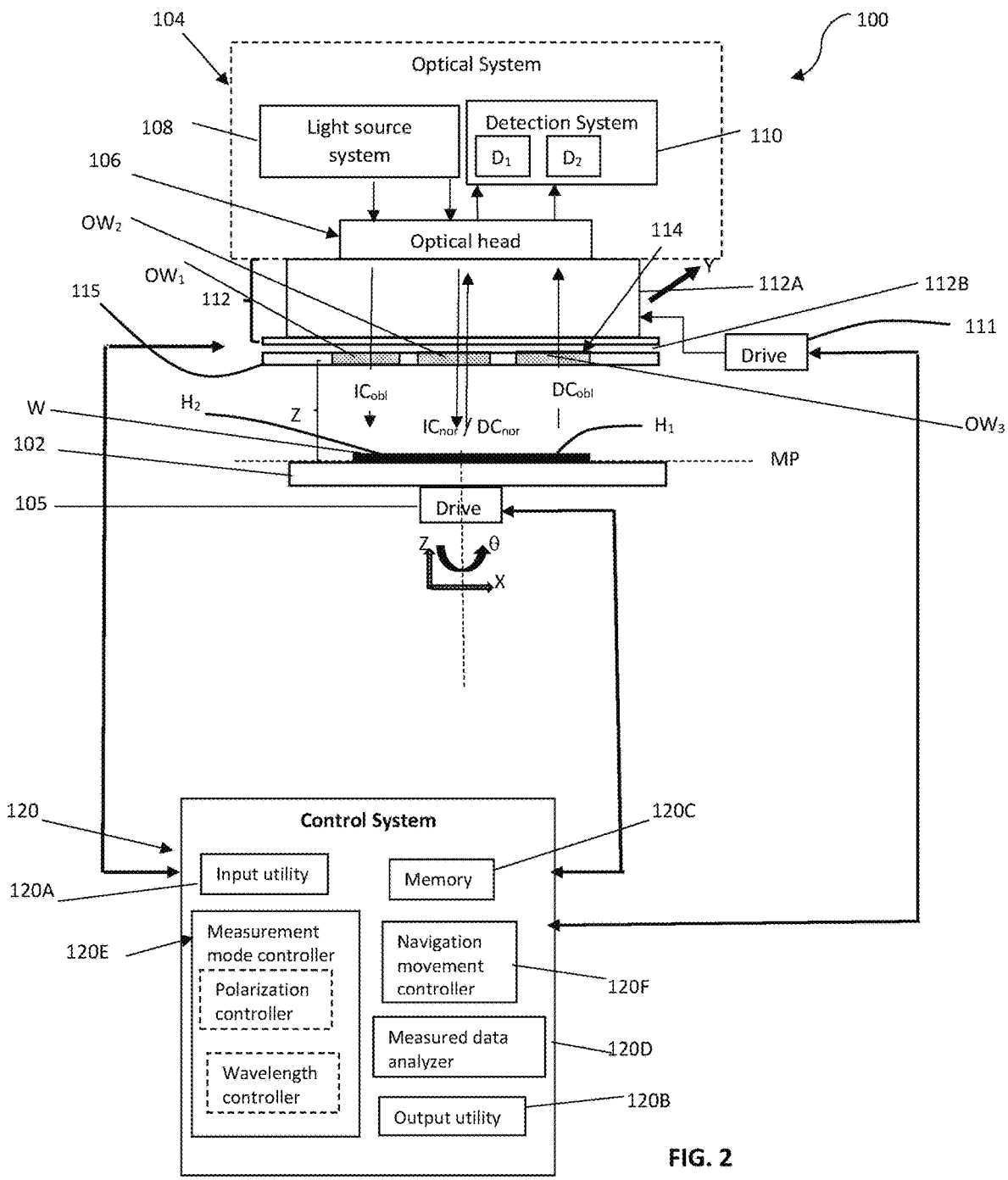
FIG. 2 schematically illustrates the configuration of an integrated measurement/metrology system according to the invention.

Reference is now made to FIG. 2 which schematically illustrates, by way of a block diagram, a measurement system 100 of the present invention, which is configured and operable enabling its integration with a processing equipment (e.g. similar to the example of FIG. 1) for applying OCD measurements to structures before and/or after being processed by processing tool(s) of the processing equipment. The measurement system 100 includes a structure support assembly 102 for holding a structure W (i.e. semiconductor wafer) under measurements and defining a measurement plane MP, an optical system 104, and a holder assembly for holding a movable part of the optical system 104.

The support assembly 102 may include a motion stage configured for movement along one or more axes in the measurement plane and a rotatable chuck assembled on the motion stage. Thus, generally speaking, the support assembly may be configured as an r, stage, which is driven, by appropriate driver(s)/motor(s) 105 for rotation in a plane parallel to the measurement plane MP and for movement along a first lateral axis, X-axis, in this plane. Such movement may be used for navigating over the structure (wafer) in order to reach measurement sites.

The support assembly 102 is also configured for adjusting a z-axis position of the measurement plane MP. As will be described more specifically further below, the z-positioning of the stage is preferably implemented using a double-wedge engine.

The optical system 104 is configured to define normal and oblique optical schemes. The optical system 104 includes an optical head 106 which is optically coupled to a light source system 108 and a light detection system 110, and comprises light directing assembly (e.g. folding mirror, lenses, etc.) defining illumination and light collection channels. The optical system may also include a polarization assembly (not shown here) enabling measurements with different polarization conditions.

It should be noted that either one or both of the light source system 108 and the light detection system 110, as the constructional (internal) part(s) of the optical system 104 within the integrated measurement system 100, may be constituted by, respectively, light output port(s) and light input ports(s), while illuminating/detection assemblies or parts thereof could be accommodated outside the integrated measurement system 100, and be optically coupled (e.g. by light guiding elements, such as fibers) with the light input and output ports. Thus, each of the blocks 108 and 110 indicating, respectively, the light source system 108 and the light detection system 110, should be interpreted broadly, not necessarily including light emitter(s) and light sensitive detector(s).

The holder assembly 112 includes a support unit (carriage) 112A configured for holding the optical head 106, and a guiding unit 112B including guiding rail(s) (not shown here) extending along a second lateral axis, Y-axis, perpendicular to the X-axis. The carriage 112A is mounted on the guiding unit 112B and driven, by a drive unit/mechanism 111, for sliding movement along the guiding rail(s).

Thus, the holder assembly 112 is actually configured and operable as a Y-stage for movement of the optical head 106 (being a movable part of the optical system 104) along the Y-axis. The structure (wafer) is moving on the x-θ stage 102. As will be described more specifically further below, the Y-stage 112 operates to move the optical head 106 including a set of objective lenses, and possibly polarizers and bending mirrors. to bring the light beams from the light source to the objective lens and to the wafer, and back.

In some embodiments, the structure under measurements may be a symmetric structure having a certain lateral dimension, e.g. a disk-like structure having a certain diameter (e.g. semiconductor wafer). A travel distance y of the optical head 106 along the Y-axis may be up to a dimension of the structure, e.g. wafer's diameter, e.g. 300 mm. The travel distance along the x-axis (i.e. during the navigation movement) may be about half-dimension of the structure, e.g. the wafer's radius, e.g. 150 mm; and the stage rotation angle θ is in a range of 0-180 degrees. This will be described further below with reference to FIG. 6A.

The system 100 also includes an optical window arrangement 114 appropriately configured for light propagation from and to the optical head 106. Such optical window arrangement 114 is formed in a plate/enclosure/frame (a so-called faceplate) 115 between the holder assembly 112 (with the optical head 106 thereon) and a measurement plane MP (wafer plane). The faceplate 115 with the optical window arrangement 114 presents an input/output light plane of the optical head.

The optical window arrangement 114 is designed to seal the moving parts (optical head 106) from the structure. The optical window arrangement 114 includes three optical windows $OW_1$, $OW_2$, $OW_3$, which are elongated, extending along the Y-axis, and which are arranged in spaced-apart parallel relationship in the faceplate 115 to be located in the illumination and collection channels. A certain distance z is maintained between the optical window arrangement 114 (i.e. input/output light plane of the optical head) and the measurement plane MP. The optical window has a length corresponding to the y-axis travel distance, which corresponds to the dimension of the structure, e.g. 300 mm diameter wafer.

As will be described more specifically further below, the central optical window $OW_2$ extends in a horizontal plane and serves for normal scheme operation of the optical system, and two other optical windows $OW_1$ and $OW_3$ extends along tilted surfaces and serve for the oblique scheme operation of the optical system.

As will also be described more specifically and exemplified further below, the optical head 106 includes an objective lens assembly. The distance between the optical head 106 and the measurement plane MP is selected to provide as small as possible distance/gap between the objective lens assembly and the measurement plane, in order to meet the requirements of the as small as possible footprint of the entire integrated measurement/metrology system and in order to reduce aberration effects induced by the optics. Accordingly, the objective lens(es) is/are short-focus lens (es).

It should also be noted that considering the integrated measurement system 100, being integrated with the processing equipment PE, e.g. as exemplified in FIG. 1, there might be a need to maintain certain environment in the vicinity of the measurement plane, i.e. in the vicinity of the structure being measured. This may be certain required environment such as $N_2$ or vacuum or $CO_2$. The invention provides for using, for this purpose, the gas supply used in the processing equipment (respective processing tool), thus eliminating a need for any additional gas source. More specifically, the gas ($N_2$) coming from the EFEM can be used without the need to use additional $N_2$ source. To this end, the interfaces of the integrated measurement system 100 and EFEM are sealed, and the wafer compartment in the integrated measurement system 100 is sealed to enable $N_2$ flow from the EFEM to the vicinity of the wafer while in the system 100.

As described above, the optical system 104 is configured to define normal and oblique optical measurement schemes for directing incident (illuminating) light along normal and oblique illumination channels onto the structure and collecting light returned from the illuminated region on the structure and propagating along respective collection channels. The returned light may include specular reflection of the illumination from structure and/or zero-order scattered light.

The optical system may also be used for dark-field measurements, while illuminating light and light being collected propagate along different channels, e.g. the same oblique illumination channel and different collection channels being used for performing both the bright- and dark-field modes. For example, the central optical window $OW_2$ is located within the coinciding/overlapping region of the optical path of the normal and oblique schemes and defines illumination and collection channels $IC_{nor}$ and $DC_{nor}$, and optical windows $OW_1$ and $OW_3$ are located at opposite sides of the central window and define, respectively, illumination and collection channels $IC_{obl}$ and $DC_{obl}$, of the oblique scheme.

For example, the optical system 104 may utilize a common light source system 108 optically coupled with the illumination channels $IC_{nor}$ and $IC_{obl}$ of the normal and oblique optical schemes, and separate detection devices $D_1$ and $D_2$ may be accommodated in the respective collection channels of the normal and oblique optical schemes.

In some embodiments, the measurement system 100 is configured for performing both imaging and measurements of the structure. Accordingly, the optical system 104 is configured such that at least one of the collection channels $DC_{nor}$ and $DC_{obl}$ defines spatially separated imaging and measurement channels/paths associated with two different detectors $D_1$ and $D_2$, being for example a CCD (imaging detector) and a spectrophotometer (measurement detector). To this end, said at least one of the collection channels $DC_{nor}$ and $DC_{obl}$ includes a light splitting device, e.g. a pinhole mirror device, for spatially separating the collected light into imaging and measurement light portions and directing them to propagate through the imaging and measurement channels/paths. For example, the measurement channels of both the normal and oblique optical schemes may be optically coupled to the same measurement detector (e.g. (spectrometer). The configuration and operation of the measurement system 100 is exemplified more specifically further below.

As further shown in FIG. 2, the measurement system 100 is configured for data communication with a control system 120, via wires and/or wireless signal transmission of any suitable technology. The control system 120 includes data input and output utilities 120A, 120B, memory utility 120C, measured data analyzer 120D.

Also provided in the control system 120 are various controllers for controlling the system operation, including a measurement mode controller 120E and a navigation movement controller 120F. The measurement mode controller 120E is configured for controlling the system shift/switch between the normal and oblique measurement modes; and may be also configured for controlling such conditions as variation of polarization and/or wavelength and/or azimuth angle, etc. The navigation movement controller 120F is configured and operable to operate the drivers 105 and 111 to control, respectively, the rotational movement of the structure support assembly 102 (e.g. chuck) and X-axis movement of the structure support assembly 102 (e.g. stage), and the movements of the optical head 106 along the Y-axes.

As described above, the rotational movement of the support assembly 102 (e.g. chuck) may be performed to implement first and second successive measurement sessions corresponding to first and second opposite angular positions of the stage 102 bringing respectively first and second halves $H_1$ and $H_2$ of the structure W into the measurement position. Each of the first and second measurement sessions may, in turn, be implemented while controlling the lateral movements of the support assembly 102 and the optical head 106 along the X- and Y-axes to thereby navigate measurements of multiple measurements sites on respective one of the first and second halves of the structure W. As described above, considering measurements on such a disk-like structure, a maximal travel distance x of the support assembly 102 along the X-axis corresponds to (is equal or slightly larger than) the radius r of the structure, and a travel distance y of the optical head along the Y-axis is up to a diameter 2r of the structure.

Generally, the integrated measurement/metrology system typically performs measurements on multiple measurement sites over the wafer. It should be understood that a manner in which a relative displacement between the wafer and the optical head is implemented depends on a sampling plan for a specific structure (e.g. for 300 mm wafer). The two-halves measurement mode described above is a non-limiting example, which can be used when the selected measurement sites are located/oriented symmetrically (assuming 180 degrees symmetry). It could be a case when other orientations of wafer/measurement sites are to be measured. In that case, the navigation (rotation and/or X-axis movement and/or Y-axis movement) could be optimized due to a number of the measurement sites and their orientation. It should also be noted that the above-described translation scheme is not the most minimized movement scheme that could cover the entire wafer (e.g. Theta/R, R), but might be optimal in some applications. The principles of the invention are not limited to the two-halves measurement mode.

Reference is made to FIGS. 3A to 3D exemplifying the configuration of the holder assembly 112 carrying the optical head part 106 (moving part) of the optical system 104.

Figures 3A, 3B:
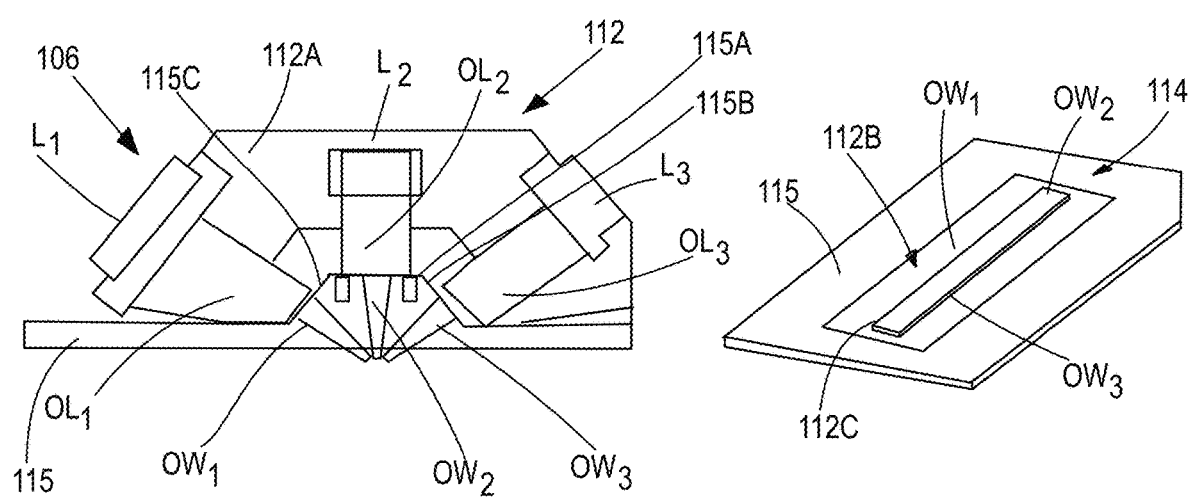
FIGS. 3A to 3C show a specific, not limiting example of the configuration of a holder assembly for holding an optical head in the optical system of the invention.

As shown in FIG. 3A, the optical head 106 has three light directing optical units (focusing optics) $L_1$, $L_2$, $L_3$ defining three light propagation paths relating to, respectively, oblique-scheme illumination channel $IC_{obl}$, illumination-and-collection channels $IC_{nor}$-and-$DC_{nor}$ of the normal optical scheme, and the detection channel $DC_{obl}$ of the oblique optical scheme. The optical units $L_1$, $L_2$, $L_3$ include objective lenses $OL_1$, $OL_2$, $OL_3$ (and possibly other optical elements), defining corresponding optical paths aligned with the optical windows $OW_1$, $OW_2$ and $OW_3$ (e.g. apertures) provided in a faceplate 115 between the holder assembly 112 and the measurement plane, where the structure being measured is located. The faceplate 115 has a planar (horizontal) facet 115A in which the optical window $OW_2$ is made, and two tilted facets 115B and 115C in which optical windows $OW_1$ and $OW_3$ are made. The optical units $L_1$, $L_2$, $L_3$ are arranged with respect to the faceplate 115 such that the light outputs/inputs of the optical units $L_1$, $L_2$, $L_3$ are aligned with the optical windows $OW_1$, $OW_2$ and $OW_3$, respectively. It should be noted that the tilted orientation of the optical windows provides 90 degrees between the optical axis of the respective lens unit and the window surface.

Figure 3C:
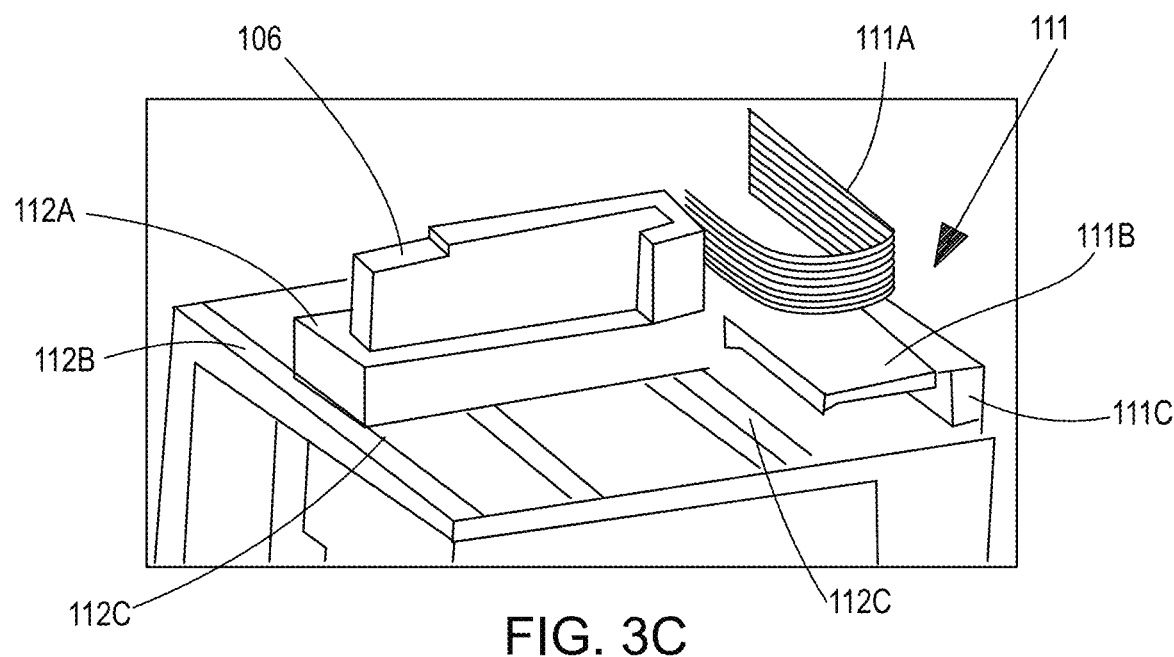

As shown in FIGS. 3A and 3C, the holder assembly 112 has the support unit 112A (optical head carriage) on which the focusing/objective optical units $L_1$, $L_2$, $L_3$ are mounted with the proper angular orientations corresponding to the optical schemes. The support unit 112A, holding the optical head 106, is mounted on the guiding unit 112B for sliding movement along guiding rail(s) 112C defining the sliding movement path along which the support unit 112A moves back and forward As described above, the holder assembly 112 (support unit 112A and guiding unit 112B) presents a Y-stage for the moving part (optical head) of the optical system 104. The optical window arrangement 114 (e.g. three-window arrangement made on the faceplate 115) is located between the holder assembly 112 and the measurement plane MP.

One window $OW_2$ is horizontal for the normal optical scheme, and two other windows $OW_1$ and $OW_3$ are tilted with respect to the horizontal plane and used for the oblique optical scheme. The Y-stage is configured to move the optical head 106 (a set of three optical units including objective lenses, and possibly also polarizers and bending (light directing) mirrors, as will be described further below) to bring the illuminating light beams from the light source to the objective lens and to the structure, and direct light returned from the structure to the detection system.

In some embodiments, the Y-stage drive 111 includes a linear magnetic motor. Preferably, the linear magnetic motor is configured such that a magnet 111A is moving and coils assembly 111B is static. This configuration provides relatively constant drive current, and heat transfer from the coils to the system boundaries, for heat dissipation via heat dissipation interface 111C. Such a requirement may be associated with the need for the stage to be very close to the optic head environment which requires temperature stability.

As described above, the objective lens is to be positioned as close as possible to the measurement plane, and therefore the optical units $L_1$, $L_2$, $L_3$ include short focus lenses. This requirement is further supported by configuring the optical window arrangement 114 with very thin optical windows to reduce boresight changes, e g 2 mm, where the window thickness is substantially uniform along the window (±1 μm tolerance), whose length is at least 2 orders higher than the thickness, e.g. about 300 mm length. Also, as described above and will be exemplified more specifically further below, the optical system 106 may include polarizers (e.g. in the optical units $L_1$, $L_2$ and $L_3$). Accordingly, the optical windows $OW_1$, $OW_2$ and $OW_3$ are configured to maintain (i.e. not affect) polarization of light passing therethrough. For example, the optical windows' media may be birefringent.

For each given position of the support assembly 102 with respect to the optical head 106, the sliding movement of the optical head 106 along the guiding rail 112C (along the Y-axis), enables measurements within an elongated region along the Y-axis of the structure W located in the measurement plane MP. After the step-movement of the stage 102 a predetermined distance in a range (0-r) along the X-axis, measurements can be applied to further region(s) of the structure W e.g. while moving optical head along the Y-axis for a distance up to 2r. Such step-by-step movements of the stage (support assembly) 102 along the X-axis and the optical head 106 (i.e. the support unit 112A) along the Y-axis enable measurements to be performed on multiple sites of the wafer. For example, one half $H_1$ of the structure W may be first inspected using the x- and y-movements of the stages 102 and 112, then, the stage 102 may be rotated by 180 degrees bringing the other half $H_2$ of the structure to the measurement position, and the process is repeated to perform measurement(s) on this half of the structure.

Figure 4A:
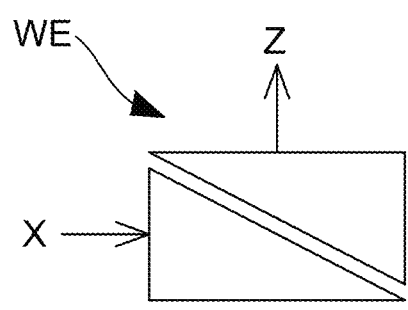
FIGS. 4A to 4D show the principles of a standard wedge design used in Z-stages to transfer X-axis motion to Z-axis motion (FIGS. 4A-4B), and a specific, not limiting example of the configuration of z-stage utilizing double wedge engine, suitable for use in the measurement system of the invention (FIGS. 4C-4D)
Figure 4B:
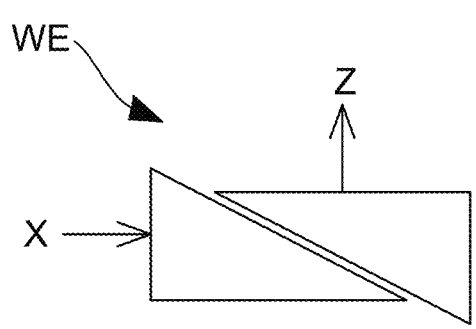
Figures 4C, 4D:
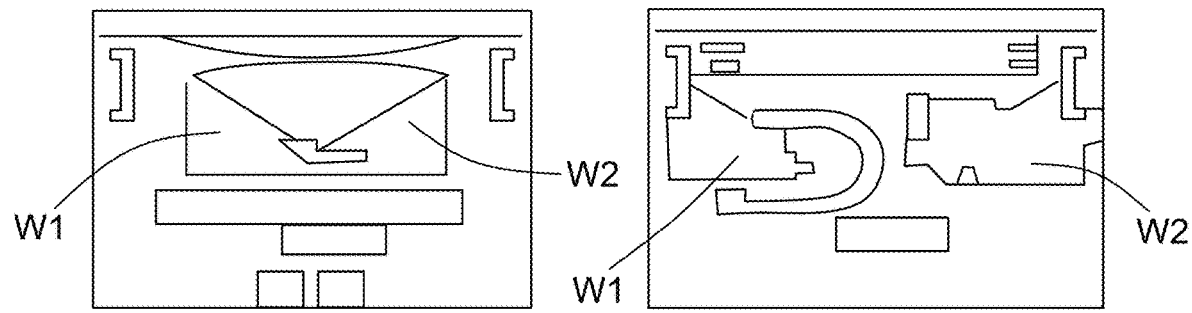

Further, z-axis position of the optical head 106 with respect to the measurement plane MP is controlled, e,g. for the focusing purposes, The z-positioning of the support assembly 102 is preferably implemented using a double-wedge engine in this connection, reference is made to FIGS. 4A-4B and 4C-4D, FIGS. 4A and 4B show a standard wedge engine (WE) design used in :Z-stage configuration to transfer X-axis motion to Z-axis motion, in, respectively z-up position ix-closed position) and z-down (x-open position), This configura_tion suffers from relatively large non symmetric foot print i.n x-dimension, when in the open position. FIGS. 4C and 4D show a specific example of the z--stage 102 utilizing a double-wedge configuration fanned by two oppositely symmetric wedges $W_1$ and $W_2$, in the z-up, x-close position (FIG. 4C) and z-down x-open position (FIG. 4D). This configuration reduces the x-dimension footprint of the system.

Figure 5:
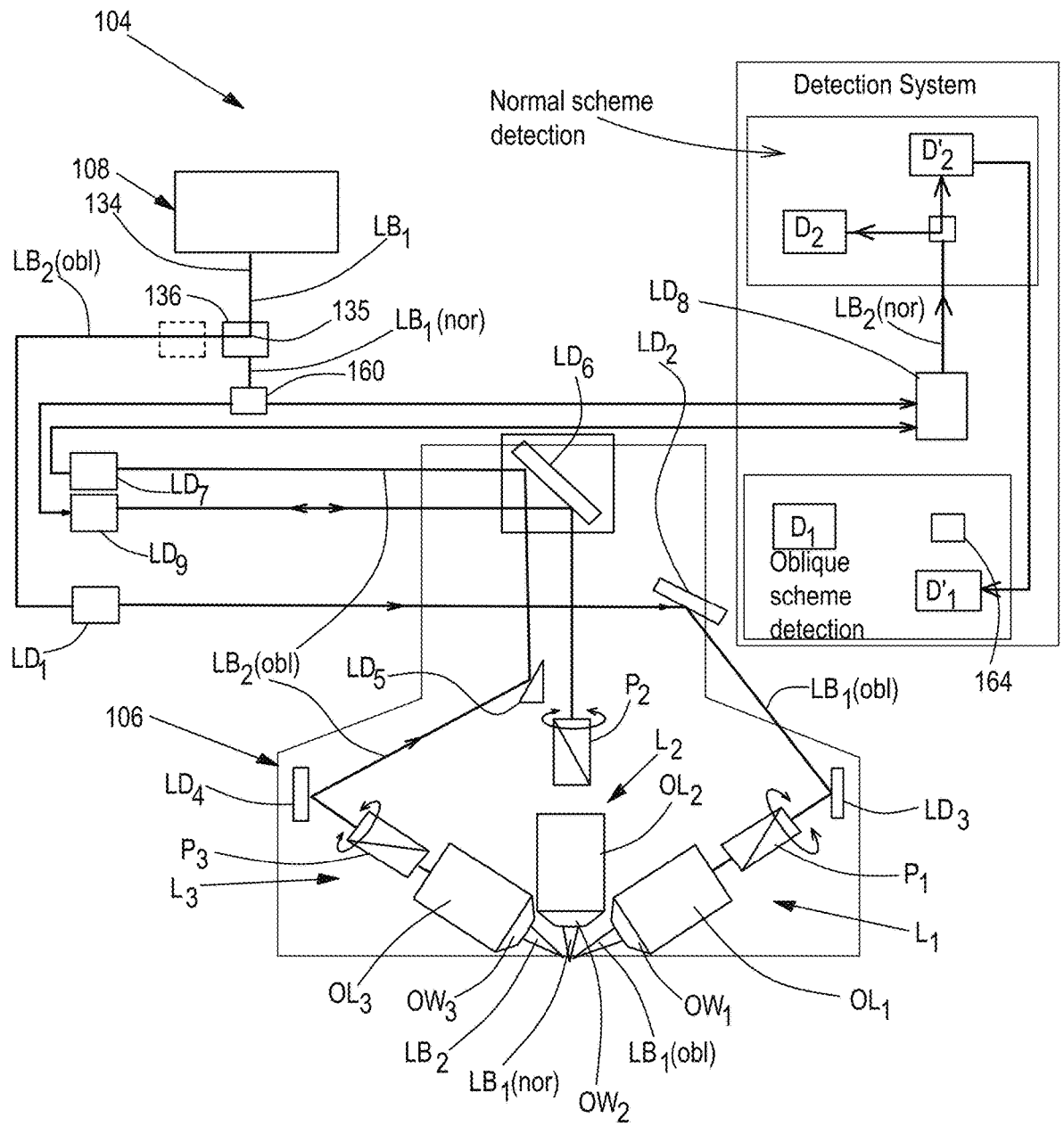
FIG. 5 illustrates a light propagation scheme in the optical system of the integrated measurement/metrology system of the invention, configured for the optical system operation with normal and oblique operational modes.

Reference is now made to FIG. 5, exemplifying the configuration and operation of the optical system 104 and a light propagation scheme therein. In the present not limiting example, a single (common) illumination assembly (light source system) 108 is used for both normal and oblique light propagation schemes. The light source system 108 may include an illuminating fiber which guides light from a light emitter to the illumination channel.

Also, in this example, switching/shifting between the normal and oblique operational modes (i.e. shifting between the light propagation in the normal and oblique schemes) is implemented by controlling a position of a shutter 136, i.e. a so-called jumping mirror. Further, in this example, the detection system 110 includes two detection assemblies associated with the normal and oblique collection channels $DC_{nor}$ and $DC_{obl}$. Each of these two detection assemblies is configured for concurrent operation with imaging and measurement modes, and include respective imaging detector units $D_1$ and $D_2$ (e.g. CCDs), and either include respective measurement detectors $D_1'$ and $D_2'$ or a common measurement detector (spectrometric detector) is used for both the normal and oblique schemes. The system operates with broadband illumination, e.g. within 210-2500 nm range. Also, in the present not limiting example, polarization assemblies are used. In the figure, the polarizers/analyzers are shown as being parts of the optical units $L_1$, $L_2$, and $L_3$ forming the optical head 106. It should, however be understood that the invention is limited to neither the use of any polarizers nor to accommodation of the polarizers within the movable part of the optical system, i.e. the optical head 106 carried by the holder assembly 112.

Thus, an illuminating light beam $LB_1$ propagates from the light source system 108 and is directed by light directing elements (e.g. illumination relay lens unit and tubular lens unit), to propagate along an input light path 134 towards a mode-shift location 135. To this end, a redirecting element 136, e.g. a mirror, is provided being controllably displaceable (e.g. by the measurement mode controller 120E) between its operative state in which it is located in the position 135 and its inoperative state being outside the light path 134.

When the mirror 136 is in its operative position, the illuminating light beam $LB_1$ interacts with the mirror 136 and is reflected by it to propagate along the illumination channel $IC_{obl}$ of the oblique scheme, and the system thus operates with the oblique mode. The illumination channel $IC_{obl}$ is optically coupled to the respective optical assembly $L_1$ of the optical head 106. As shown in the specific not limiting example of FIG. 5, the illumination channel $IC_{obl}$ may include one or more light directing (light path bending) elements, e.g. mirrors—three such light directing elements (mirrors) $LD_1$, $LD_2$, $LD_3$ being shown in the present example. As further shown in the figure, the optical assembly/unit $L_1$ includes a lens unit (one or more lenses), and also includes a polarizer $P_1$, which is thus located in the oblique-scheme illumination channel $IC_{obl}$. The so-created oblique-incident polarized illuminating light beam $LB_1^{(obl)}$ is focused onto an illuminating region on the structure via the respective optical window $OW_1$. Light $LB_2^{(obl)}$ returned from the region illuminated by the light beam $LB_1^{(obl)}$ is collected by the optical assembly $L_3$ via the optical window $OW_3$, where the polarization of light is adjusted by a respective polarizer $P_3$, and the collected returned light is directed to propagate along the oblique-scheme detection channel $DC_{obl}$. Similarly, this detection channel $DC_{obl}$ may include one or more light directing elements (e.g. mirrors)—five such elements $LD_4$-$LD_8$ being shown in this schematic illustration. The element $LD_8$ may be configured as a wedge prism with two reflecting facets, that re-directs light incident thereon, depending on the light incidence position. Thus, element $LD_8$ directs the oblique-reflection light beam $LB_1^{(obl)}$ to propagate towards the oblique-scheme detection assembly to interact with a split element 164 (e.g. pinhole mirror) where this beam is split into imaging and measurement components propagate along two spatially separated imaging and detection channels $C^{(obl)}_{imag}$ and $C^{(obl)}_{meas}$ associated with imaging and measurement detectors (or respective light input ports) $D_1$ (e.g. CCD) and $D'_1$ (spectrometer).

When the element 136 is in its inoperative position (being moved to be outside the light path 134), the illuminating light beam $LB_1$ passes the location 135 and interacts with a beam splitter 160 which directs (reflects in the present example) the illuminating light beam $LB_1$ to propagate along the illumination channel $IC_{nor}$ of the normal scheme, and the system thus operates with the normal mode. The illumination channel $IC_{nor}$ is optically coupled to the respective optical assembly/unit $L_2$ (objective lens unit $OL_2$) of the optical head 106. The normal illumination channel $IC_{nor}$ may include light directing elements, e.g. mirrors. As exemplified in the figure, the configuration is such that the normal illuminating light beam $LB_1$ successively interacts with the light directing elements (mirrors) $LD_9$ and $LD_6$ and enters the optical unit $L_2$, which includes objective lens(es) and a polarizer $P_2$ to focus polarized normal-incidence light beam $LB_1^{(nor)}$ onto the same region on the structure via the optical window $OW_2$. Light $LB_2^{(nor)}$ returned from the region illuminated by the light beam $LB_1^{(nor)}$ is collected by optical window $OW_2$ to pass through the optical unit $L_2$ and directed to propagate along the same path along the normal-scheme light collection channel $DC_{nor}$, where the light beam is directed by successive interactions with light directing elements (mirrors) $LD_6$, $LD_9$ and $LD_8$, and the latter directs the beam $LB_2^{(nor)}$ towards a split element (pinhole mirror) 162, which directs two split portions of the light beam $LB_2^{(nor)}$ to propagate along spatially separated imaging and measurement detection channels towards normal-scheme imaging detector/light input port $D_2$ (e.g. CCD) and a light input port $D_2$ optically coupled with the measurement detector. As mentioned above, the same measurement detector (spectrometer) may be used for detecting light of both the normal and oblique optical schemes.

It should be noted that the measurement system of the present invention is not limited to splitting both the normal and oblique scheme collection channels into the two detection channels. For example, each of these collection channels may use a single detection channel/single detector; or one of the normal and oblique scheme collection channels may include two different detection schemes, while the other does not. Moreover, the different detection schemes may be different in the type of detections (e.g. as exemplified above, for detecting imaging and non-imaging data); and/or may be different in detection of different spectral ranges.

Figure 6A:
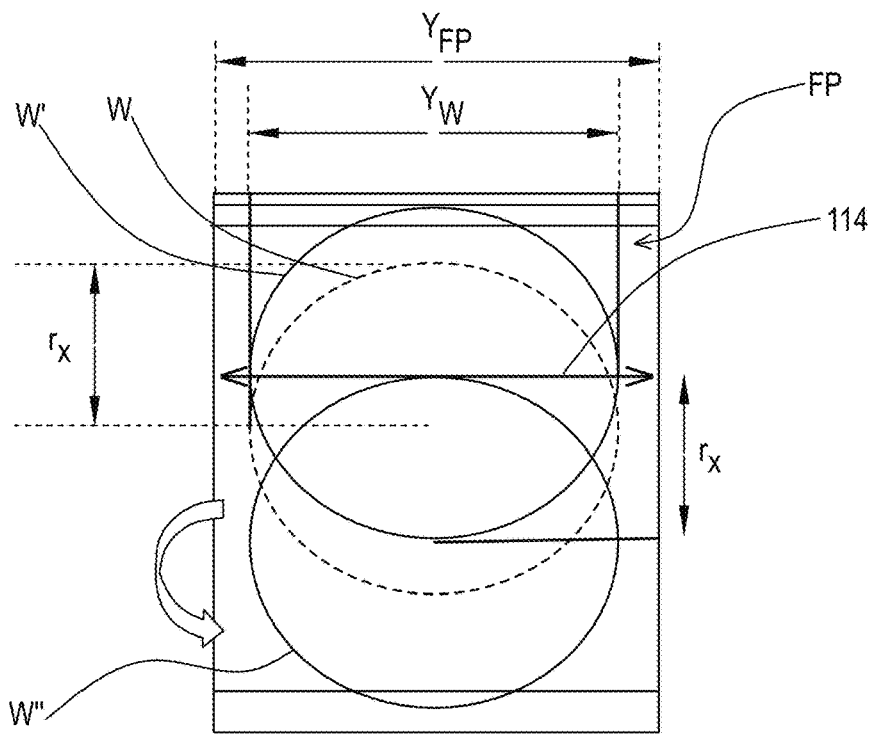
FIG. 6A shows schematically a top view of an exemplary integrated measurement system of the invention, illustrating traveling ranges of the optical window and wafer (support assembly) within the footprint of the system.
Figure 6B:
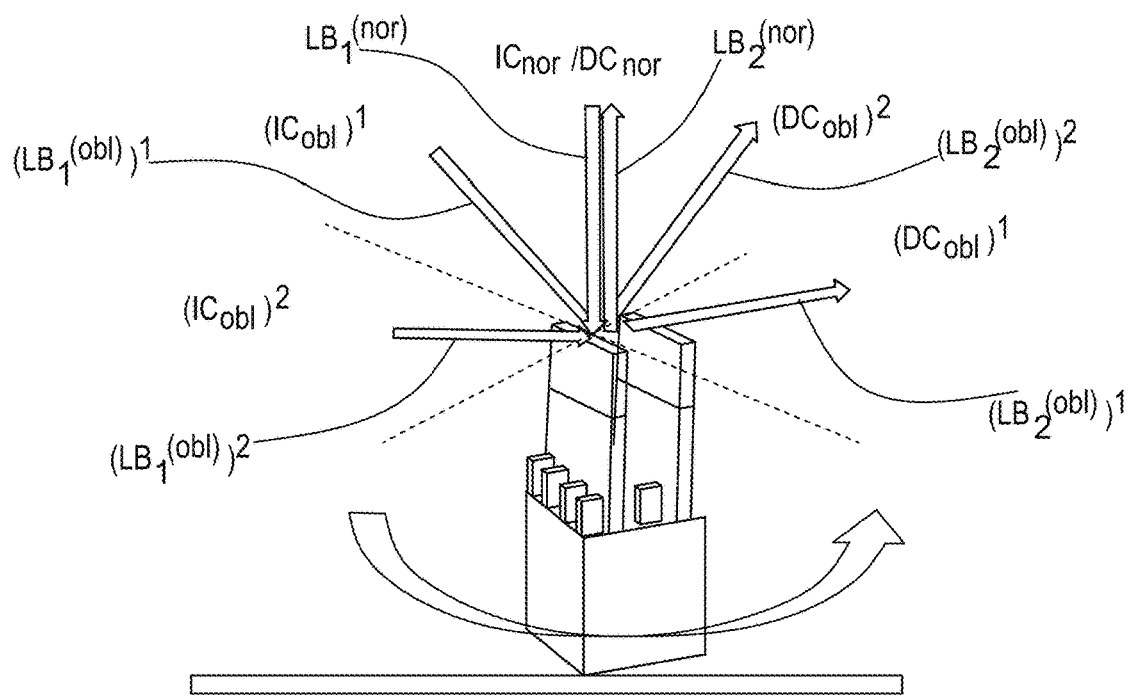
FIG. 6B illustrates a typical geometry of a complex patterned structure being measured in a wafer, showing that the system configuration of the present invention enables measurements with a larger number of available azimuths (per pattern) for oblique mode and polarization azimuths for normal mode.

Reference is made to FIGS. 6A and 6B showing some other features of the invention. As described above, in some embodiments, the integrated measurement system has a small footprint, e.g. less than 500 mm² which does not allow to scan a 300 mm wafer in X- and Y-directions. On the other hand, a patterned structure being measured on the wafer (as shown in FIG. 6B) has no rotation symmetry relative to oblique channel. Therefore, the structure may be measured in multiple sites thereof by displacement of the optical head along the Y-axis (via movement of the support unit 112A of the holder assembly 112), and displacing the structure along the X-axis and rotation the structure in the measurement plane (via respective movements of the support assembly 102). This is exemplified in FIG. 6A, which shows schematically a top view of the integrated measurement system of the invention, illustrating the optical window 114 and structure/wafer W traveling ranges within the footprint FP of the system. FIG. 6A shows the structure W having radius $r_x$ (e.g. 150 mm of the 300 mm-diameter wafer), in its load position, and two displaced positions W' and W" corresponding to, respectively, displacement of the structure along the X-axis and rotation of the structure in the measurement plane, resulting from the X-axis movement and rotation of the support assembly 102. The travel distance $Y_W$ of the optical head along the Y-axis is up to the structure's diameter 2r, (e.g. 300 mm, considering a semiconductor wafer or a somewhat larger distance, e.g. 302-304 mm) within the Y-axis footprint dimension $Y_{FP}$. The travel distance along the X-axis may be about half-dimension of the structure, e.g. the wafer's radius, e.g. 150 mm (or a slightly larger distance, e.g. 154 mm). The structure's support assembly 102 rotates the structure W in the measurement plane with a rotation angle θ in a range of 0-180 degrees. Thus, by moving the optical head along the Y-axis and the structure's support assembly along the X-axis, and rotation of the support assembly, the structure can be measured half-by-half in multiple sites via the optical window arrangement 114 using either one or both of the normal and oblique measurement schemes, as described above.

Referring to FIG. 6B, there is schematically illustrated combination of normal and oblique measurement schemes applied to a complex patterned structure W. Due to the above-described system configuration, i.e. handling, transfer and rotation of the structure being measured and the optical head movement range, the present invention allows measurements with a larger number of available azimuths (per pattern) for oblique mode and polarization azimuths for normal mode. This figures exemplifies the normal measurement scheme defined by illumination and detection channels $IC_{nor}$ and $DC_{nor}$ for propagation of illuminating and specularly reflected light beams $LB_1^{(nor)}$ and $LB_2^{(nor)}$. The figure also shows two different oblique measurement schemes, defined, respectively, by illumination and detection channels $(IC_{obl})^1$–$(DC_{obl})^1$ and $(IC_{obl})^2$–$(DC_{obl})^2$, corresponding two 0-degree and 90-degree azimuth angles, obtained via rotation of the structure in the measurement plane with respect to the optical system. Structures/patterns on the wafer breaks azimuth symmetry except for the angular range 0-180.

Thus, the present invention provides a novel relatively simple solution for optical measurement system operable with both normal and oblique optical schemes, and enabling the system configuration with reduced footprint to be properly integrated with the processing equipment.

We claim:

1. A measurement system configured for integration with a processing equipment for applying optical measurements to a structure, the measurement system comprising:
  a support assembly for holding a structure under measurements in a measurement plane, the support assembly being configured and operable for rotation in a plane parallel to the measurement plane and for movement along a first lateral axis in said measurement plane;

an optical system defining illumination and collection light channels of normal and oblique optical schemes;

the optical system comprising an optical head comprising at least three lens units located in the illumination and collection channels;

a holder assembly comprising: a support unit for carrying the optical head, and a guiding unit configured and operable for guiding a sliding movement of the support unit along a path extending along a second lateral axis perpendicular to said first lateral axis;

and an optical window arrangement comprising at least three optical windows made in a faceplate located between the optical head at a certain distance from the measurement plane, the at least three optical windows being arranged in spaced-apart parallel relationship and extending parallel to said path, said at least three optical windows being aligned with the illumination and collection channels for, respectively, propagation of illuminating light from the optical head and propagation of light returned from an illuminated region to the optical head, in accordance with said normal and oblique optical schemes.

2. The measurement system according to claim 1, further comprising a controller configured and operable for controllably shifting the optical system operation between the normal and oblique optical schemes.

3. The measurement system according to claim 1, wherein the optical system comprises a common illumination assembly optically coupled with the illumination channels of the normal and oblique optical schemes, and separate detection devices accommodated in the respective collection channels of the normal and oblique optical schemes.

4. The measurement system according to claim 1, wherein the. optical head comprises at least three objective lens units located in, respectively, the normal and oblique optical schemes.

5. The measurement system according to claim 1, wherein the at least three optical windows are configured to maintain polarization of light passing therethrough.

6. The measurement system according to claim 1, wherein the faceplate has a planar facet in which a central one of the at least three optical windows is made, and two tilted side facets at opposite sides of the planar facet in which two other of the at least three optical windows are made, such that each of the at least three optical windows is located in a plane of 90 degrees orientation with respect to an optical axis of one of the least three lens units.

7. The measurement system according to claim 1, wherein said support assembly is configured and operable by a driving mechanism to control a position of the measurement plane with the respect to the optical head.

8. The measurement system according to claim 7, wherein said driving mechanism comprises a double-wedge engine.

9. The measurement system according to claim 1, wherein the optical system comprises a polarizing assembly comprising at least one polarizer located in at least one of the illumination and collection channels.

10. The measurement system according to claim 9, wherein the polarizer assembly is located within the optical head and comprises three polarizers located in, respectively, illumination and detection channels of the normal and oblique optical schemes.

11. The measurement system according to claim 1, wherein each of the at least three optical windows has a length which is at least two orders of magnitude higher than (a) a maximal thickness of the optical window and (b) a minimal thickness of the window.

12. The measurement system according to claim 11, wherein the maximal thickness of the optical window is two millimeters.

13. The measurement system according to claim 1, wherein the light returned wherein each of the collection channels is configured for directing the light returned to spatially separated imaging and measurement channels.

14. The measurement system according to claim 13, wherein each of the collection channels comprises a pinhole mirror device for spatially separating the collected light into imaging and measurement light portions and directing them to propagate through imaging and measurement channels.

15. The measurement system according to claim 14, wherein said imaging and measurement channels are optically coupled to imaging and measurement detection devices.

16. The measurement system according to claim 15, wherein the measurement channels of the normal and oblique optical schemes are optically coupled to a shared spectrometric detector.

17. The measurement system according to claim 1, further comprising a navigation movement system configured and operable to drive rotational movement of the support assembly and the movements of the support assembly and the support unit of the holder assembly along said first and second lateral axes, respectively.

18. The measurement system according to claim 17, wherein navigation movement system comprises a drive assembly configured and operable for driving the sliding movement of the support unit of the holder assembly along a guiding rail of the guiding unit.

19. The measurement system of claim 18, wherein said drive assembly comprises a linear magnetic motor.

20. The measurement system according to claim 19, wherein the linear magnetic motor comprises a movable magnet and a static coils assembly.

21. A measurement system configured for integration with a processing equipment for applying optical measurements to a structure, the measurement system comprising:

a support assembly defining a measurement plane for holding a structure under measurements in the measurement plane, the support assembly being configured and operable as an x-Theta stage;

an optical system configured with normal and oblique optical measurement schemes and comprising an optical head and light directing elements for directing incident light from a light source to the optical head and directing light collected by the optical head to a detection system;

a holder assembly configured and operable as a y-stage for guiding a sliding movement of the optical head along an y-axis; and an optical window arrangement comprising at least three optical windows made in a faceplate located between the optical head and the measurement plane at a certain distance from the measurement plane, the at least three optical windows being arranged in spaced-apart parallel relationship and extending along the y-axis, providing propagation of illuminating light from the optical head and propagation of light returned from an illuminated region to the optical head, in accordance with said normal and oblique optical measurement schemes of the optical head.

* * * * *